(12) United States Patent
McDaniel et al.

(10) Patent No.: US 9,622,883 B2
(45) Date of Patent: Apr. 18, 2017

(54) LONG BONE RESURFACING BONE LOCK

(71) Applicant: Biomet Manufacturing, LLC, Warsaw, IN (US)

(72) Inventors: John M. McDaniel, Warsaw, IN (US); Nathan A. Winslow, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 15/166,794

(22) Filed: May 27, 2016

(65) Prior Publication Data

US 2016/0270932 A1    Sep. 22, 2016

Related U.S. Application Data

(62) Division of application No. 14/215,898, filed on Mar. 17, 2014, now Pat. No. 9,351,836.

(60) Provisional application No. 61/791,825, filed on Mar. 15, 2013.

(51) Int. Cl.
| | |
|---|---|
| *A61F 2/28* | (2006.01) |
| *A61F 2/38* | (2006.01) |
| *A61F 2/46* | (2006.01) |
| *A61F 2/30* | (2006.01) |

(52) U.S. Cl.
CPC ........ *A61F 2/4637* (2013.01); *A61F 2/30749* (2013.01); *A61F 2002/30387* (2013.01); *A61F 2002/30579* (2013.01); *A61F 2002/30884* (2013.01); *A61F 2002/464* (2013.01); *A61F 2002/4642* (2013.01); *A61F 2220/0033* (2013.01)

(58) Field of Classification Search
CPC .......... A61F 2/3859; A61F 2/38; A61F 2/389; A61F 2/4637; A61F 2/30749; A61F 2/40
See application file for complete search history.

(56) References Cited

U.S. PATENT DOCUMENTS

| | | | |
|---|---|---|---|
| 5,800,557 | A | 9/1998 | Elhami |
| 9,351,836 | B2 | 5/2016 | McDaniel et al. |
| 2003/0212457 | A1 | 11/2003 | Martin |
| 2006/0064173 | A1 | 3/2006 | Guederian |
| 2007/0282450 | A1 | 12/2007 | Habermeyer et al. |
| 2010/0125333 | A1 | 5/2010 | Zdeblick et al. |
| 2010/0241236 | A1 | 9/2010 | Katrana et al. |
| 2014/0277566 | A1 | 9/2014 | McDaniel et al. |

OTHER PUBLICATIONS

"U.S. Appl. No. 14/215,898, Non Final Office Action mailed Oct. 1, 2015", 11 pgs.

(Continued)

*Primary Examiner* — Jason-Dennis Stewart
(74) *Attorney, Agent, or Firm* — Schwegman Lundberg & Woessner, P.A.

(57) ABSTRACT

A locking implant is provided for a long bone. The locking implant comprises a head portion, a stem portion extending from the head portion, and an anchor disposed at an end of the stem portion for engagement within a resected long bone. The anchor defines at least one locking feature, such as a cam, configured to engage an interior of the resected long bone upon rotation of the implant, thereby locking the head portion to the long bone. The implant may comprise a two component modular design. Methods of locking the implant to along bone structure are also provided.

5 Claims, 8 Drawing Sheets

(56) References Cited

OTHER PUBLICATIONS

"U.S. Appl. No. 14/215,898, Notice of Allowance mailed Feb. 1, 2016", 9 pgs.
"U.S. Appl. No. 14/215,898, Response filed Sep. 11, 2015 to Restriction Requirement mailed Jul. 30, 2015", 7 pgs.
"U.S. Appl. No. 14/215,898, Response filed Dec. 29, 2015 to Non Final Office Action mailed Oct. 1, 2015", 12 pgs.
"U.S. Appl. No. 14/215,898, Restriction Requirement mailed Jul. 30, 2015", 7 pgs.

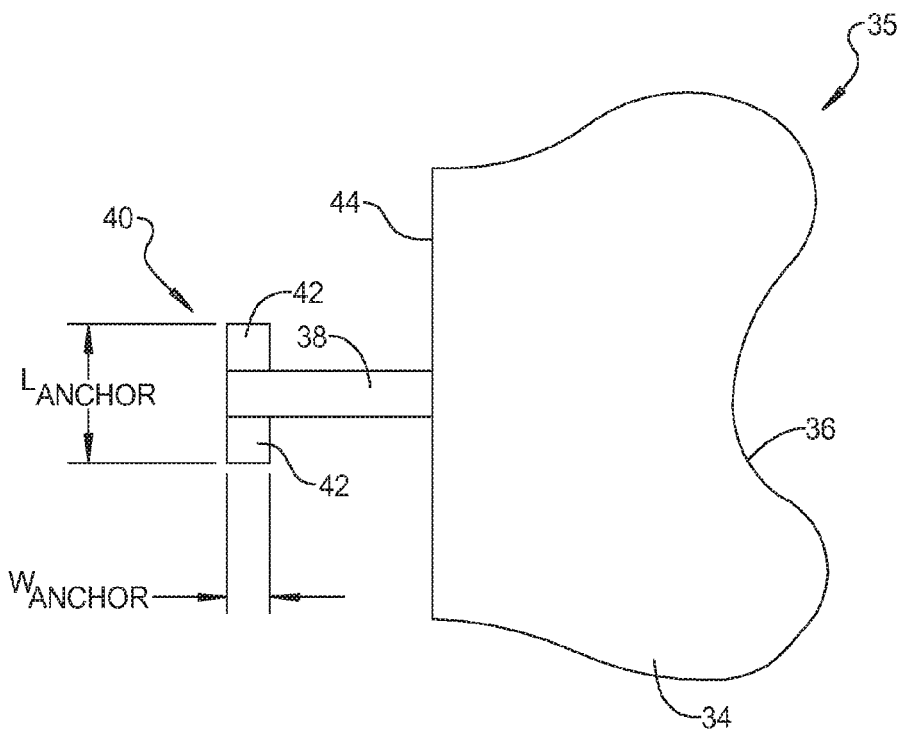
FIG 7
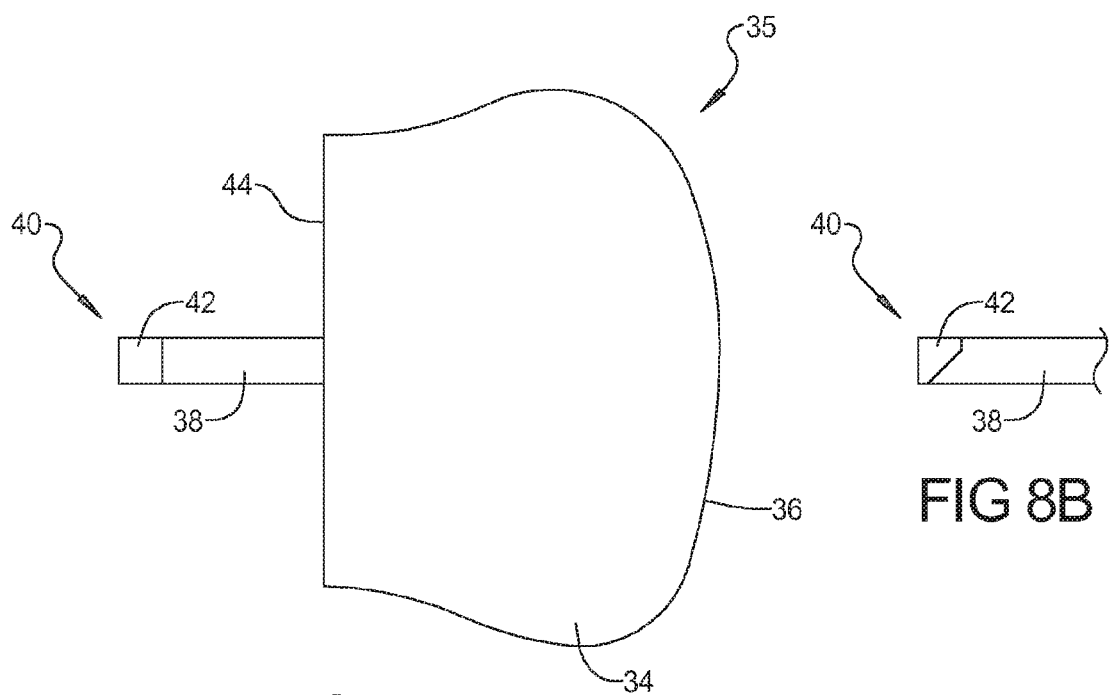
FIG 8A
FIG 8B

LONG BONE RESURFACING BONE LOCK

CROSS-REFERENCE TO RELATED APPLICATIONS

This application claims the benefit of U.S. Provisional Application No. 61/791,825, filed on Mar. 15, 2013. The entire disclosure of the above application is incorporated herein by reference in its entirety.

FIELD

The present disclosure relates to anatomical implants, such as long bones having modular joints.

BACKGROUND

This section provides background information related to the present disclosure which is not necessarily prior art.

Stabilization of long bones following fractures, malformations, and other situations including trauma and arthritis, can sometimes be treated non-surgically with splints, injections, and medications. In other cases, surgery may be required. Surgical options include fusion and joint replacement. Fusion can relieve pain and restore pinch strength; however, motion in the joint is lost. Joint implants can be used to restore joint motion. While current joint implants are suitable for their intended use, they are subject to improvement. For example, there is a need for a joint implant having improved modularity, enhanced sizing options, and enhanced options with respect to degree of joint constraint.

SUMMARY

This section provides a general summary of the disclosure, and is not a comprehensive disclosure of its full scope or all of its features.

In various aspects, the present teachings provide a locking implant for a long bone. The locking implant comprises a head portion, a stem portion extending from the head portion, and an anchor disposed at an end of the stem portion for engagement within a resected long bone. The anchor defines at least one locking feature, such as a cam, configured to engage an interior of the resected long bone upon rotation of the implant, thereby locking the head portion to the long bone.

The present teachings further provide a modular joint implant assembly. The implant assembly comprises a base component having first and second ends. The first end defines a first anchor for engagement with an aperture defined in a resected long bone. The second end defines a second anchor. A head component is provided, defining at least one retaining feature configured to couple to the second anchor of the base component. The first anchor defines at least one locking feature configured to engage an interior of the resected long bone upon rotation of the base component, thereby locking the base component to the long bone.

The present teachings also provide for a method of locking an implant to a long bone structure. The method comprises excising a defective end of the long bone. A transverse slot is cut in the long bone distally extending a distance from a resection line. The method includes inserting a stem and anchor portion of the implant through the slot from a side of the long bone. The method proceeds with rotating the implant and locking the anchor to an interior of the long bone.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The present teachings will become more fully understood from the detailed description and the accompanying drawings, wherein:

FIG. 7 is a cross-sectional view of the locking implant of FIG. 5 taken along the line A-A;

FIG. 8A is a cross-sectional view of the locking implant of FIG. 5 taken along the line B-B;

FIG. 8B is a partial cross-sectional view of a wedge shaped stem portion that can be used with FIG. 5;

Figure 1:
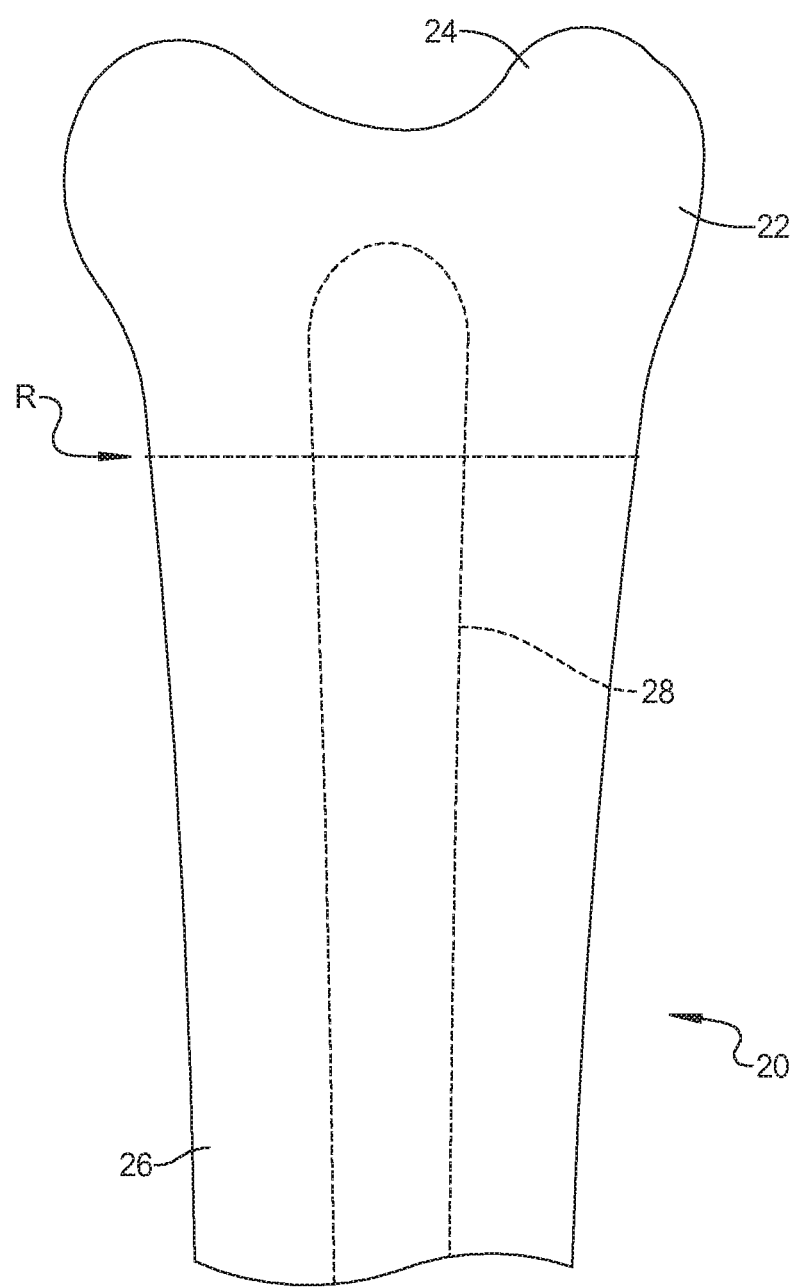
FIG. 1 is a partial side plan view of a long bone requiring a resection in accordance with the present teachings.

Corresponding reference numerals indicate corresponding parts throughout the several views of the drawings. It should be noted that the figures set forth herein are intended to exemplify the general characteristics of materials, methods, and devices among those of the present technology, for the purpose of the description of certain aspects. These figures may not precisely reflect the characteristics of any given aspect, and are not necessarily intended to define or limit specific embodiments within the scope of this technology. Further, certain aspects may incorporate features from a combination of figures.

DETAILED DESCRIPTION

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The following description of technology is merely exemplary in nature of the subject matter, manufacture, and use of one or more inventions, and is not intended to limit the scope, application, or uses of any specific invention claimed in this application or in such other applications as may be filed claiming priority to this application, or patents issuing therefrom.

Figure 5:
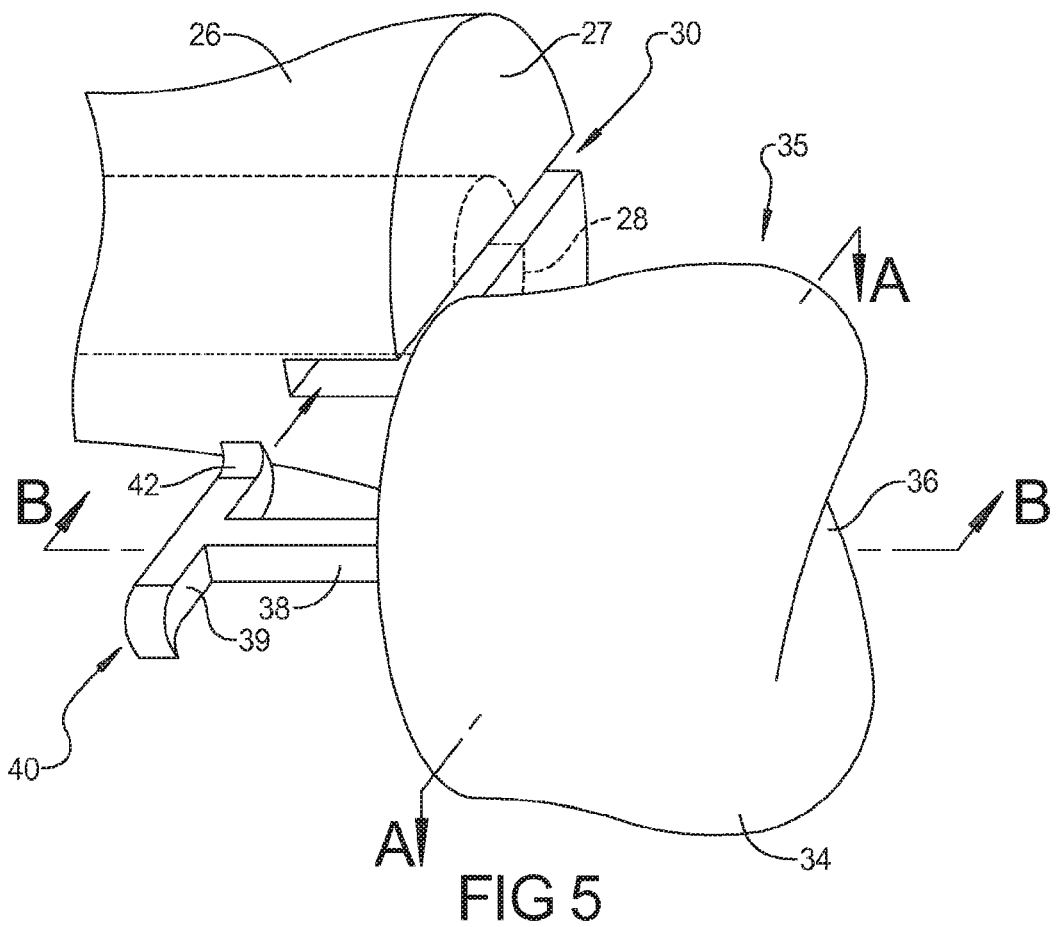
FIG. 5 is a side perspective view of a stem and anchor of a locking implant being inserted into a side of the long bone through the transverse extending slot.
Figure 6:
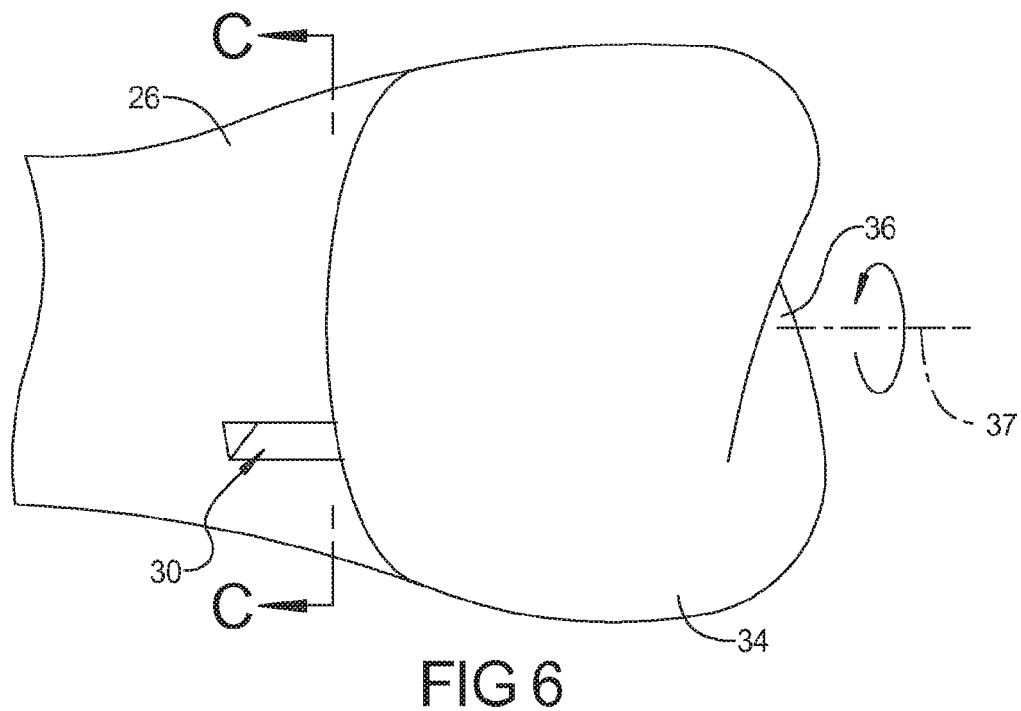
FIG. 6 is a side perspective view illustrating the rotation of the locking implant with respect to the long bone.

The present technology generally relates to medical implant components and methods for improving the procedures for implanting medical devices and bone fracture repairs. As used herein, the term "implant" may be used to refer to an entire implant, or a portion thereof; portions may be as large or as small as necessary to accommodate the specific need. For example, an implant made in accordance with the present disclosure, generally including a head portion with a stem and anchor as shown in FIG. 5, may constitute the entire implant, or it may be used with one or more pieces or components that together form a final implant or implant assembly. The present disclosure encompasses a wide variety of therapeutic and cosmetic applications, for human and/or other animal subjects, and the specific materials, devices, and instruments used should be biomedically acceptable. As used herein, such a "biomedically acceptable" or "biocompatible" material or component is one that is suitable for use with humans and/or animals without undue adverse side effects (such as toxicity, irritation, and allergic response) commensurate with a reasonable benefit risk/ratio.

The terminology used herein is for the purpose of describing particular example embodiments only and is not intended to be limiting. It should be noted that the term "user" may refer to a surgeon or any one of a number of individuals who assist the surgeon during a bone fracture repair procedure. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath", "below," "lower," "above," "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Various aspects of the present teachings provide a locking implant assembly for use with a bone or joint of a human or animal subject. Although many features of the technology are disclosed and illustrated herein pertaining to a long bone articulation, it is envisioned that the present technology is also applicable for use with various other articulations, such as the digits of the hand and foot, as well as the tibial plateau, and other joints. Accordingly, the present teachings should not be limited to certain bones or types of implants. Various known implant designs include a stem portion having a wide or tapered diameter designed to be inserted into a cavity defined in the bone, such as an intramedullary canal, and press-fit or cemented therein. By way of example, with the insertion of a radial head implant, this often requires a surgeon to dislocate the joint in order to implant the stem into the cavity. The present teachings eliminate the use of a press-fit stem, and allow a surgeon to insert an implant from a side of the bone, without dislocating the bone joint, while still providing a locking engagement between the implant and the bone.

Figure 2:
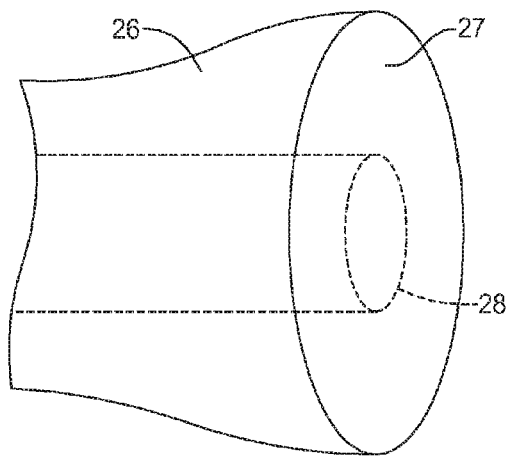
FIG. 2 is a partial side perspective view of the resected long bone of FIG. 1.
Figure 3:
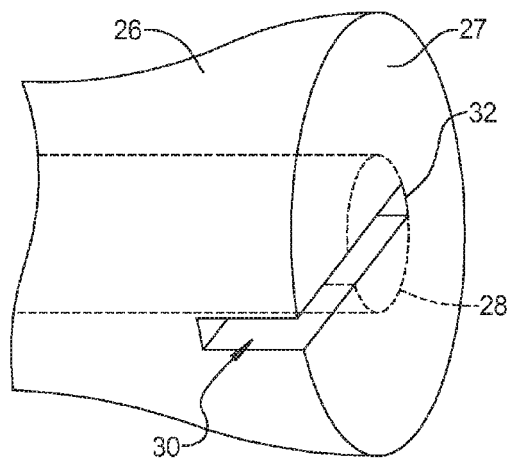
FIG. 3 is a partial side perspective view of the resected long bone of FIG. 1 defining a transverse extending slot partially extending across the long bone.
Figure 4:
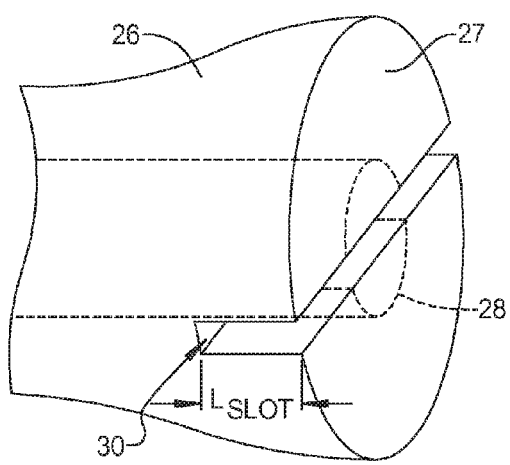
FIG. 4 is a partial side perspective view of the resected long bone of FIG. 1 defining a transverse extending slot fully extending across the long bone.

With initial reference to FIG. 1, a long bone 20 is provided illustrating the need for a resection along line R to excise at least an end portion 22 of the long bone 20, including an articulation surface 24. After the defective joint articulation, or end portion 22, is excised as shown in FIG. 2, a shaft 26 of the long bone 20 is left with a substantially planar exposed edge 27, and in certain aspects, at least partially exposing a portion of either an intramedullary canal 28 or area of spongy bone, depending on the particular bone and the location of the resection line R. FIG. 3 illustrates the cutting of a transverse slot 30 into at least a portion of the shaft 26 of the long bone 20, with the innermost portion of the slot 30 abutting an outer area or wall 32 of the intramedullary canal 28. FIG. 4 illustrates the transverse slot 30 extending across the entire shaft 26. As shown, the slot 30 distally extends a distance from the resection line R, or exposed edge 27, into the shaft 26 in a longitudinal direction of the long bone as designated by the reference $L_{slot}$ shown in FIG. 4. In various aspects, the length of the slot $L_{slot}$ is substantially equal to a length of a stem portion 38, discussed below.

With reference to FIG. 5, in various aspects, the locking implant 35 may have a shape and size commensurate with the excised end portion 22 of the long bone, defining a similar articulating surface 36. The locking implant 35 may include a head portion 34, a stem portion 38 extending from the head portion 34, and an anchor 40 disposed at a distal end 39 of the stem portion 38, configured for engagement within the resected long bone shaft 26. The head portion 34 may define an upper articulating surface 36 and a substantially planar lower surface 44, as best shown in FIGS. 7 and 8A, which are cross-sectional views taken along the lines A-A and B-B of FIG. 5, respectively. The lower planar surface 44 is preferably configured to matingly engage with the planar edge 27 of the shaft 26. The stem portion 38 may orthogonally extend from the lower planar surface 44, and the locking feature 42 of the anchor 40 may radially extend a distance from the stem portion 38. FIG. 8B is another configuration of the stem portion having an anchor locking feature 42 that is provided with an angled wedge shape that can be used to cut into and wedge into the bone. As should be understood, modifications of the above configurations can be, including changes to the dimensions, geometries, and spatial relationship of the various components that together form the implant 35.

In various aspects, the anchor 40 defines at least one locking feature 42 configured to engage and/or wedge with an interior of the resected long bone shaft 26 upon rotation of the implant 35, thereby locking the head portion 34 to the edge 27 of the long bone shaft 26. In certain aspects, a friction fit may be provided to encourage long term fixation of the implant 35 in the bone. The locking feature 42 may define a cam or wedge surface that, upon rotation of the implant, grippingly engages the interior of the resected long bone shaft 26. The cam surface may include teeth or sharp protrusions extending from a portion thereof. In other aspects, the locking feature 42 can include at least one of an extending pin, curved hook, sharpened edge, protrusion, blade, nail, and annular flange.

At least one of the stem portion 38 and the anchor 40 may comprise a polymer, porous metal, and/or a porous metal coating such as Regenerex® Porous Titanium Construct to promote bone in-growth, which may enhances fixation to the long bone. Regenerex® is offered by Biomet of Warsaw, Ind. Suitable metals include, for example, CoCr, titanium, stainless steel, alloys, ceramics, and combinations thereof. Suitable polymers include, for example, one or more of ultra-high molecular weight polyethylene, pyrocarbon, silicone, polyether ether ketone ("PEEK"), carbon fiber reinforced PEEK (such as PEEK-OPTIMA® from Invibio, Ltd. of the United Kingdom), and/or vitamin E stabilized highly crosslinked polyethylene (HXLPE), such as is disclosed in U.S. Pat. No. 7,431,874 to Muratoglu et al., issued on Oct. 7, 2008.

Figure 9:
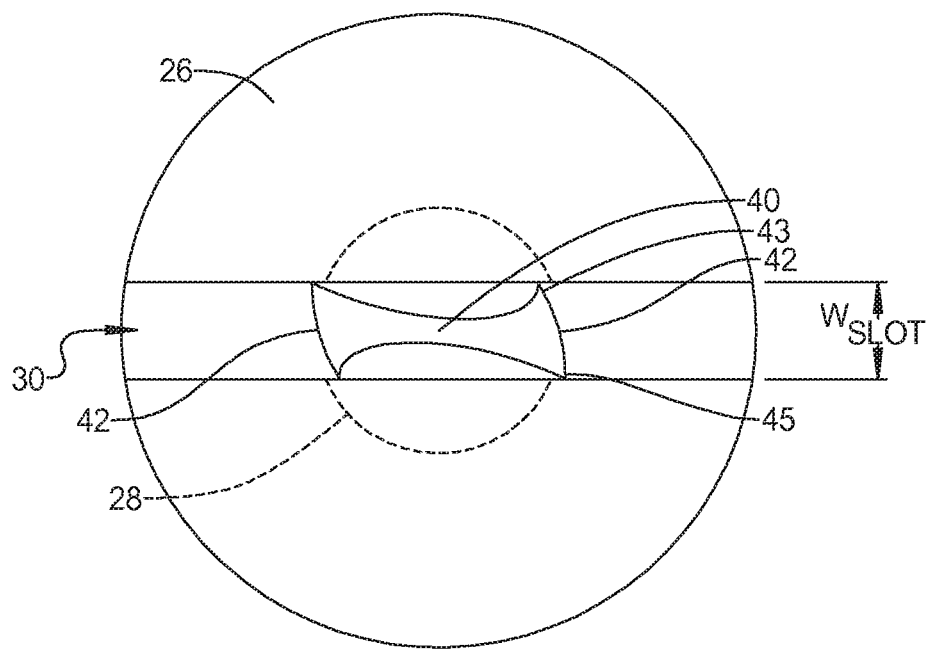
FIG. 9 is a cross-sectional view of FIG. 6 taken along the line C-C prior to the locking implant being rotated.
Figure 10:
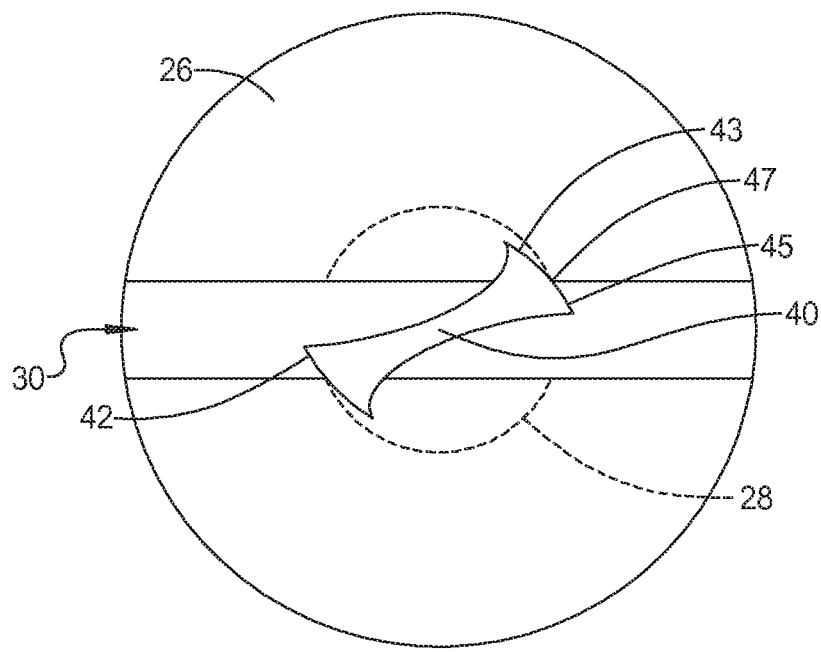
FIG. 10 is a cross-sectional view of FIG. 6 taken along the line C-C subsequent to the locking implant being rotated.

With renewed reference to FIG. 5, after the transverse slot 30 is cut or otherwise defined in the shaft 26, the methods of the present teachings include aligning the implant 35 such that the anchor 40 slides through the slot 30 from a side of the long bone shaft 26. Once fully aligned, the implant 35 is rotated along an axis 37 with respect to the long bone shaft 26 in order to lock the anchor 40 to an interior region of the long bone 26. In various aspects, the implant 35 is rotated less than about 90 degrees, less than about 60 degrees, less than about 45 degrees, and in certain aspects, less than about 30 degrees. As best shown in FIGS. 7 and 9, the anchor is provided with a width $W_{Anchor}$ and a length $L_{Anchor}$ greater than the width $W_{Anchor}$, and the width $W_{Anchor}$ of the anchor is less than a width of the slot $W_{slot}$. In certain aspects, the length of the anchor $L_{Anchor}$ is substantially equal to or greater than a diameter of the intramedullary canal 28 of the long bone shaft 26. With reference to FIG. 9, one or more sides of the locking feature 42 may have an angled cam surface with first pointed end, or tooth, 43 slightly inside of the intramedullary canal 28 and a second end 45 slightly outside of the intramedullary canal 28. When rotated, as shown in FIG. 10, the anchor 40 may be wedged and lodged in the intramedullary canal 28 and the bone, for example, at about a mid-point 47 of the cam surface locking feature 42. In various aspects, the cam surface grippingly engages the interior or intramedullary canal 28 of the resected long bone.

Figure 11:
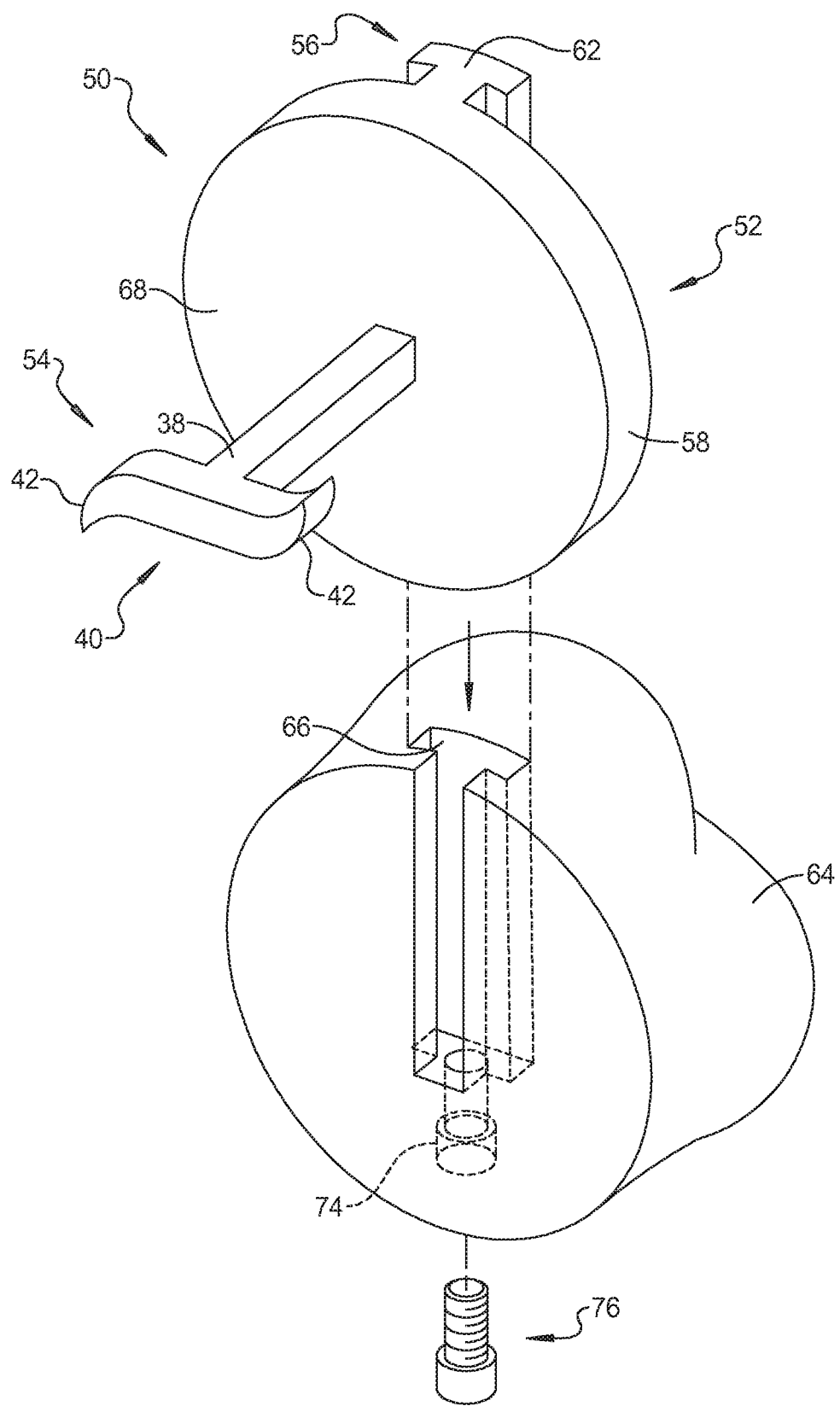
FIG. 11 is a perspective view of a modular, two component implant in accordance with the present teachings.
Figure 12:
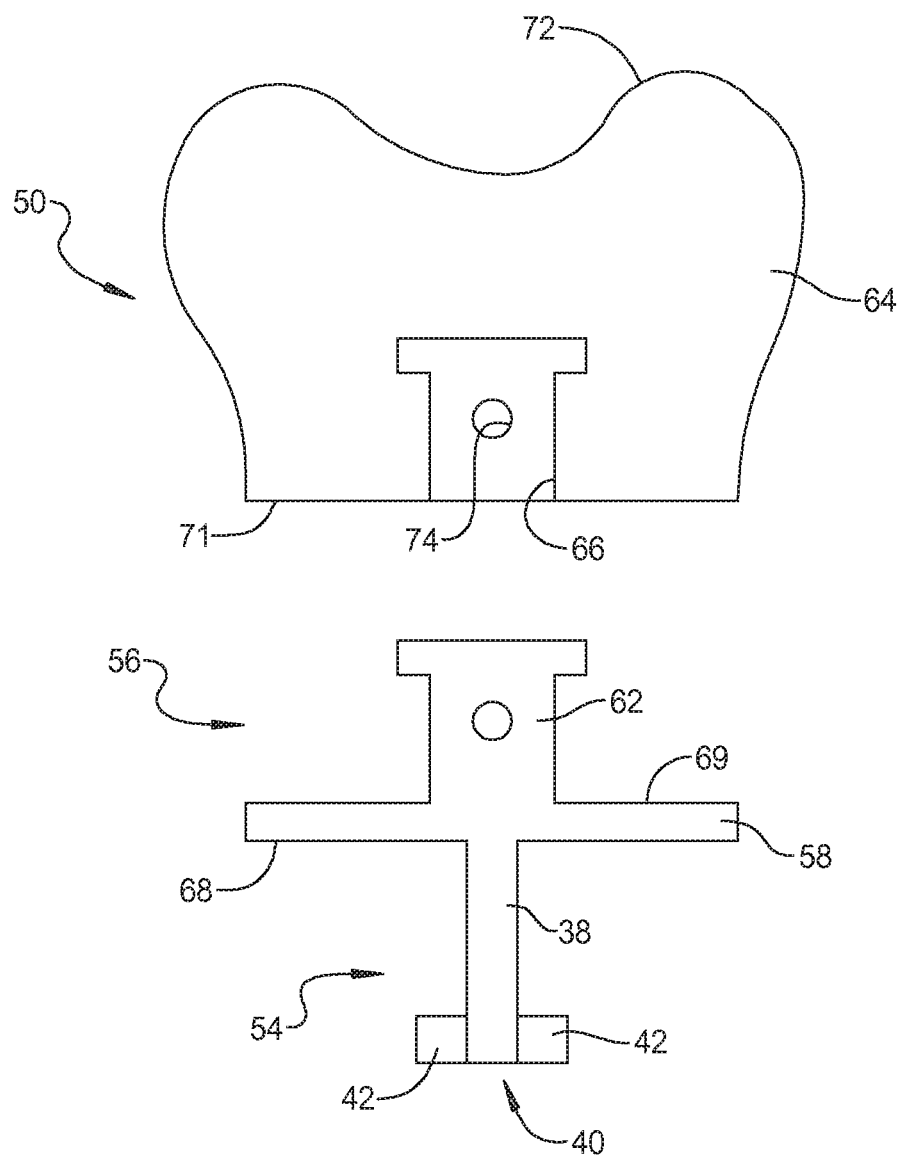
FIG. 12 is a side plan view of the modular implant components of FIG. 11.
Figure 13:
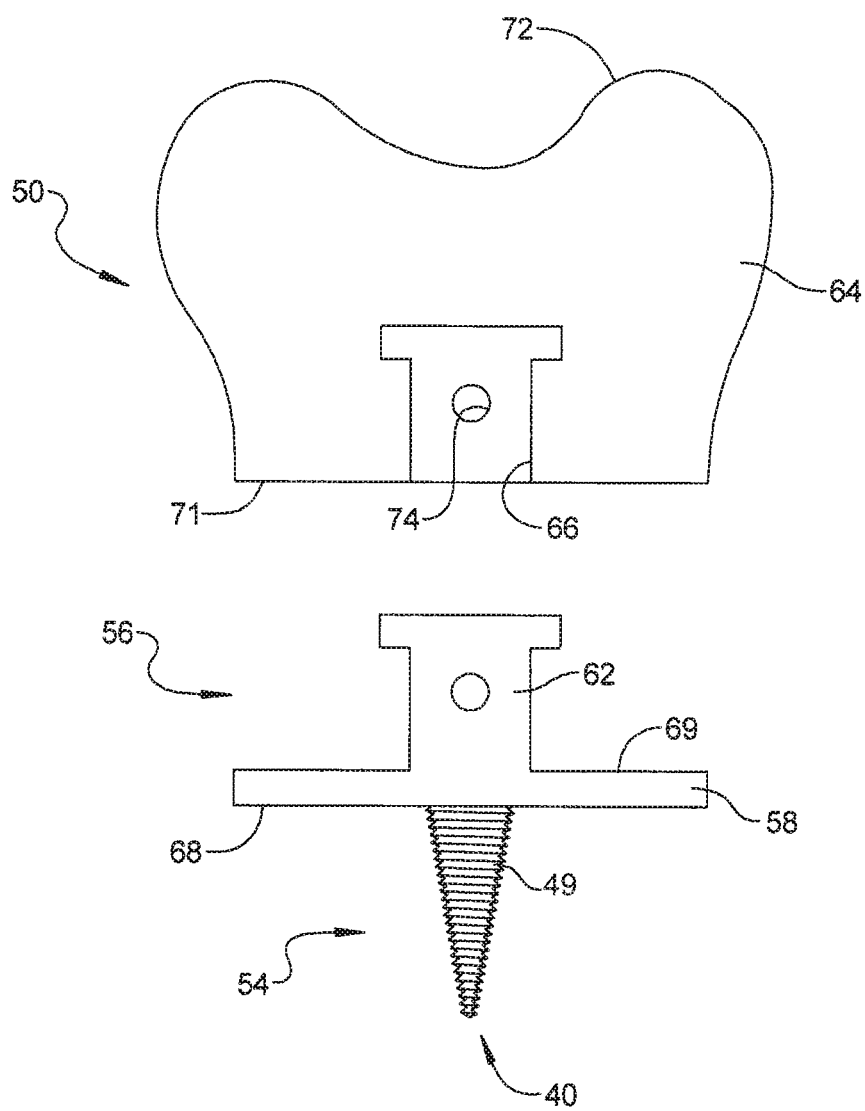
FIG. 13 is a side plan view of another modular, two component implant.

FIG. 11 is a perspective view of a modular, two component implant in accordance with the present teachings, and FIG. 12 is a side plan view of the modular implant components of FIG. 11. As shown, in certain aspects the modular joint implant assembly 50 includes a base component 52 having first and second opposing ends 54, 56. The first end 54 defines a stem portion 38 and a first anchor 40 commensurate with the stem and anchor of the unitary implant 35, including at least one locking feature 42 for engagement with an aperture, or slot 30, defined in the resected long bone shaft 26. The second end 56 defines a second anchor 62. The base component 52 may include an annular collar 58 disposed between the first and second anchors 40, 62. The modular implant assembly 50 also includes a head component 64 defining at least one retaining feature 66 configured to couple to the second anchor 62 of the base component 52. The annular collar 58 may define an upper planar surface 69 having a cross-sectional shape substantially aligned with a cross-sectional shape of a bottom surface 71 of the head component 64, and a lower planar surface 68 having a cross-sectional shape substantially aligned with the planar edge 27 of the bone shaft 26. The head component 64 may define an upper articulating surface 72 and at least one fastening bore 74. In various aspects, the second anchor 62 comprises an extended rail or dovetail-shaped flange or locking taper that cooperates with a similarly shaped retaining feature 66 of the head component 64. A mechanical fastener, such as a threaded pin or screw 76, can be optionally provided to removably couple and/or secure the base component 52 to the head component 64. Additional details of another modular assembly can be found in U.S. Pat. No. 8,303,666 issued on Nov. 6, 2012, incorporated by reference herein in its entirety. FIG. 13 is a side plan view of another design that can be used with the modular implant components of FIG. 11, which replaces the stem portion 38 and first anchor 40 with a threaded locking mechanism 49 that can be inserted into and provided in a locking arrangement with the intramedullary canal 28.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A method of locking an implant to a long bone structure, the method comprising:
    excising a defective end of the long bone;
    cutting a transverse slot in the long bone distally extending a distance from a resection line;
    inserting a stem and anchor portion of the implant through the slot from a side of the long bone;
    rotating the implant and locking the anchor to an interior of the long bone.

2. The method of claim 1, wherein the stem of the implant defines a length, and cutting the transverse slot comprises defining a slot have a length in a longitudinal direction of the long bone substantially equal to the length of the stem.

3. The method of claim 1, comprising rotating the implant a predetermined distance less than about 90 degrees with respect to the long bone.

4. The method of claim 1, wherein the anchor defines a cam surface and rotating the implant comprises grippingly engaging the cam surface to an intramedullary canal.

5. The method of claim 1, wherein the implant comprises a two component modular design including a base component removably coupled to a head component.

\* \* \* \* \*